(12) United States Patent
Bui et al.

(10) Patent No.: US 8,551,460 B2
(45) Date of Patent: *Oct. 8, 2013

(54) ENHANCED SHINE AND MOISTURE LIP COMPOSITION

(75) Inventors: Hy Si Bui, Piscataway, NJ (US);
Mohamed Kanji, Edison, NJ (US);
Anita Chon Tong, Westfield, NJ (US)

(73) Assignee: L'Oreal, Paris (FR)

( * ) Notice: Subject to any disclaimer, the term of this patent is extended or adjusted under 35 U.S.C. 154(b) by 47 days.

This patent is subject to a terminal disclaimer.

(21) Appl. No.: 12/825,633

(22) Filed: Jun. 29, 2010

(65) Prior Publication Data

US 2010/0330017 A1 Dec. 30, 2010

Related U.S. Application Data

(60) Provisional application No. 61/221,265, filed on Jun. 29, 2009.

(51) Int. Cl.
*A61K 8/00* (2006.01)
*A61K 8/18* (2006.01)
*A61K 31/74* (2006.01)
*A61Q 1/04* (2006.01)
*A61Q 1/06* (2006.01)

(52) U.S. Cl.
USPC .......................... 424/64; 424/78.03

(58) Field of Classification Search
USPC ................................. 424/64, 78.03
See application file for complete search history.

(56) References Cited

U.S. PATENT DOCUMENTS

| | | | |
|---|---|---|---|
| 6,482,400 B1 * | 11/2002 | Collin | 424/70.6 |
| 2004/0223986 A9 * | 11/2004 | Boussouira et al. | 424/401 |
| 2006/0188459 A1 * | 8/2006 | Heinrichs et al. | 424/63 |
| 2007/0031361 A1 | 2/2007 | Herrmann et al. | |

FOREIGN PATENT DOCUMENTS

| | | | |
|---|---|---|---|
| DE | 100 64 799 | | 6/2002 |
| WO | WO 01/17485 | * | 3/2001 |
| WO | WO 2006/127883 | | 11/2006 |
| WO | WO 2007/048672 | * | 5/2007 |
| WO | WO 2007/096400 | * | 8/2007 |
| WO | WO 2007/139812 | | 12/2007 |
| WO | WO 2008/046763 | * | 4/2008 |

OTHER PUBLICATIONS

Bergbreiter et al. Tet. Lett., 1997, 38 (21), 3703-3706.*
European Search Report issued Mar. 21, 2011, in European Application No. 10167792.0.
U.S. Appl. No. 13/133,176, filed Jun. 7, 2011, Bui, et al.
U.S. Appl. No. 13/133,181, filed Aug. 1, 2011, Bui, et al.
U.S. Appl. No. 12/825,707, filed Jun. 29, 2010, Bui, et al.
U.S. Appl. No. 12/825,767, filed Jun. 29, 2010, Bui, et al.
U.S. Appl. No. 12/825,807, filed Jun. 29, 2010 Bui, et al.
U.S. Appl. No. 12/825,587, filed Jun. 29, 2010, Bui, et al.
U.S. Appl. No. 12/825,840, filed Jun. 29, 2010, But, et al.
U.S. Appl. No. 12/825,623, filed Jun. 29, 2010, Bui, et al.
U.S. Appl. No. 12/825,726, filed Jun. 29, 2010, But, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,730, filed Jun. 29, 2010, Bui, et al.
U.S. Appl. No. 12/825,614, filed Jun. 29, 2010, Bui, et al.
U.S. Appl. No. 12/825,600, filed Jun. 29, 2010, Bui, et al.
U.S. Appl. No. 12/825,559, filed Jun. 29, 2010, Bui, et al.
U.S. Appl. No. 13/379,691, filed Dec. 21, 2011, Bui, et al.

* cited by examiner

*Primary Examiner* — Fereydoun G Sajjadi
*Assistant Examiner* — Genevieve S Alley
(74) *Attorney, Agent, or Firm* — Oblon, Spivak, McClelland, Maier & Neustadt, L.L.P.

(57) ABSTRACT

The present invention is directed to enhanced shine and moisturizing aqueous lip compositions with a unique texture and feel. The compositions include: (a) at least one sugar silicone surfactant; (b) at least one polyamine; (c) at least one high carbon polar modified polymer; and (d) water.

22 Claims, No Drawings

ENHANCED SHINE AND MOISTURE LIP COMPOSITION

CROSS-REFERENCE TO RELATED APPLICATIONS

This application claims the benefit of priority from U.S. Provisional Application Ser. No. 61/221,265, filed Jun. 29, 2009, the entire contents of which are hereby incorporated by reference.

FIELD OF THE INVENTION

The present invention generally relates to novel lip compositions. More particularly, the present invention relates to lip compositions having high gloss which also hydrate and moisturize the lips.

BACKGROUND OF THE INVENTION

The problem with conventional lip make up products is their inability to continuously hydrate and moisturize the lips. The reason for this is that water either has to be deposited onto the lips from the gloss itself or drawn to the lips from the atmosphere. In the event that the source of water for hydration is the product itself, it is very difficult to maintain the water in a stabilized form. Failure to do so results in the water quickly evaporating from the surface of the lips leaving the lips feeling dry.

Also, conventional lip compositions which impart a high degree of gloss onto the lip surface require the presence of silicone fluids in the composition. Silicone fluids are known to have high refractive indices which provide shine. These types of silicone fluids, however, have poor environmental profiles and, because they are relatively expensive, add to the overall cost of the product.

Therefore, it is desirable to provide lip compositions, having a high degree of gloss, which are capable of hydrating and/or moisturizing the lips in a continuous manner.

BRIEF SUMMARY OF THE INVENTION

A first aspect of the present invention is directed to cosmetic composition that is moisturizing and/or hydrating. The compositions include: (a) at least one sugar silicone surfactant; (b) at least one polyamine; (c) at least one oil-soluble high carbon polar modified polymer; and (d) water.

The present invention also relates to moisturizing, hydrating and refreshing compositions. The compositions include: (a) a reaction product of at least one polyamine and at least one high carbon oil-soluble polar modified polymer; (b) at least one sugar silicone surfactant; and (c) water.

The present invention also relates to a composition made by combining:
(a) at least one polyamine;
(b) at least one oil-soluble high carbon polar modified polymer;
(c) at least one sugar silicone surfactant; and
(d) water.

A second aspect of the present invention is directed to a method of applying the above-disclosed composition onto the lips.

It has been surprisingly found that compositions according to the present invention impart glossy, non-sticky, hydration and moisturization onto lips.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

In accordance with the present invention, the "hardness" of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf, including all ranges and subranges therebetween.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the i and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinilty of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil-soluble high carbon polar modified polymer(s) represent from about 1% to about 20% of the total weight of the composition, more preferably from about 3% to about 17% of the total weight of the composition, and most preferably from about 5% to about 15%, including all ranges and subranges therebetween.

Sugar Silicone Surfactant

According to the present invention, compositions comprising at least one sugar silicone surfactant are provided. The sugar silicone surfactant of the present invention has the following formula:

Sach-X-Dn-X-Sach where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosyl sucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula R2SiO, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, lactobionolactonesiloxane, or a mixture thereof.

Preferably, the sugar silicone surfactant represents from about 0.5% to about 20% of the total weight of the composition, more preferably from about 1% to about 18% of the total weight of the composition, and most preferably from about 3% to about 15%, including all ranges and subranges therebetween.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. Nos. 5,530,092 and 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 20% by weight, more preferably from about 0.2 to about 10% by weight, more preferably from about 0.5 to about 5% by weight, based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Water

The composition of the present invention can also contain water. The water is typically present in an amount of from about 5% to about 60% by weight, such as from about 10% to about 50% by weight, such as from about 25% to about 35% by weight, including all ranges and subranges therebetween, all weights being based on the total weight of the composition.

According to particularly preferred embodiments, sufficient water is present to form a water-in-oil emulsion.

Optional Ingredients

Non-Volatile Solvent

The cosmetic composition of the present invention can optionally further comprise at least one non-volatile solvent. As used herein, the term "non-volatile" means having a boiling point of greater than about 100° C. The at least one non-volatile solvent typically comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

The at least one non-volatile solvent, if present, is present in the cosmetic composition of the invention in an amount of from about 10% to about 90% by weight, such as from about 20% to about 75% by weight, such as from about 25% to about 65% by weight, all weights based on the total weight of the composition.

The composition of the present invention may also include other ingredients. Examples thereof include, but are not limited to, colorants such as pigments and dyestuffs, co-solvents, plasticizers, preservatives, fillers, active ingredients, additional waxes and sunscreens.

It has surprisingly been discovered that the association of a sugar silicone surfactant with the above-described polar modified polymer results in the formation of a stable emulsion capable of imparting high gloss onto the lips, in the absence of any conventional silicone fluids used to provide shine. Finally, the resultant composition, when applied onto the lips, both hydrates and moisturizes the lips dues to the large amount of water entrapped therein, while at the same time making the lips feel unusually refreshed and pleasant.

The present invention is further described in terms of the following non-limiting examples. Unless otherwise indicated, all parts and percentages are on a weight-by-weight percentage basis.

EXAMPLES

Two cosmetic compositions were prepared containing the below-disclosed ingredients.

Example 1

| Phase | Chemical Name | Example 1 |
| --- | --- | --- |
| A | Non-volatile Solvent | Q.S. |
| A | Polyethylene 400 | 8.00 |
| A | $C_{26-28}$ a-olefin-maleic acid anhydride copolymer wax | 7.00 |
| A | Pigment | 3.50 |
| A | Mica | 2.00 |
| B | Deionized Water | 22.50 |
| B | PEI-35 | 0.25 |
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent, polyethylene 400, and Oil-soluble high carbon polar modified polymer.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A were transferred to a Silverson mixer for emulsification while maintaining the temperature at 85-90 Celsius degrees.
5. In a separate beaker 2, glycerin, sugar silicone surfactant and PEI-35 were added into DI water, mixed and heated to 85 Celsius degrees.
6. The contents of side beaker B were added dropwise into the beaker A while emulsifying at 9000 rpm under the Silverson mixer for 30 minutes. Afterward, the emulsification speed was lowered to 2000 rpm for 5 minutes.
7. The contents were poured into lipstick molds at 80 Celsius degrees.
8. The lipstick in molds was placed in a cooling tunnel for 15 minutes at −10 Celsius degrees. Once cooled, the lipstick in molds were removed from the cooling tunnel to equilibrate to 25 Celsius degrees and removed from the molds after lipsticks had thawed to 25 Celsius degrees.

Example 2

| Phase | Chemical Name | Example 2 |
| --- | --- | --- |
| A | Non-volatile Solvent | Q.S. |
| A | $C_{26-28}$ a-olefin-maleic acid anhydride copolymer wax | 7.00 |
| A | Pigment | 3.50 |
| A | Mica | 2.00 |
| B | Deionized Water | 40.00 |
| B | PEI-35 | 0.25 |
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent and Oil-soluble high carbon polar modified polymer.
When enough solids had melted, the contents were mixed with moderate speed until all solids had melted at 95 Celsius degrees.
The temperature was slightly lowered to 85 Celsius degrees and pigments and mica were added.
2. The contents of main beaker A were transferred to a Silverson mixer for emulsification while maintaining the temperature at 85-90 Celsius degrees. In a separate beaker 2, glycerin, sugar silicone surfactant and PEI-35 were added into DI water and mixed and heated to 85 Celsius degrees.
3. The contents of side beaker B were added dropwise into the beaker A while emulsifying at 9000 rpm under the Silverson mixer for 30 minutes. Afterward, the emulsification speed was lowered to 2000 rpm for 5 minutes until the contents were cooled to 25 Celsius degrees.
4. The contents of main beaker A was poured into container.

What is claimed is:
1. A composition comprising:
(a) at least one sugar silicone surfactant;
(b) a water-insoluble half acid and half amide crosslinked reaction product of (1) at least one oil-soluble high carbon polar modified polymer comprising at least one C22-C40 monomer and modified with at least one hydrophilic unit, and having a weight-average molecular weight of less than or equal to 30000 g/mol and a crystallinity of 8% to 60% and (2) at least one polyamine, wherein the reaction product forms a matrix capable of entrapping water; and
(c) water,
wherein the composition is in the form of an emulsion and wherein water is entrapped within the matrix.

2. The composition of claim 1, further comprising at least one non-volatile oil in an amount ranging from 10% to 60% by weight of the total weight of the composition.

3. The composition of claim 1, wherein the sugar silicone surfactant is gluconamidoethylaminopropylsilicone.

4. The composition of claim 1, wherein the sugar silicone surfactant is present in an amount of from about 0.5 to about 25% by weight, based on the weight of the composition.

5. The composition of claim 2, wherein the sugar silicone surfactant is present in an amount of from about 0.5 to about 25% by weight, based on the weight of the composition.

6. The composition of claim 1, wherein the at least one polyamine is a branched polyalkyleneimine 7. The composition of claim 1, wherein the polyamine is present in an amount of from about 0.05 to about 20% by weight, based on the weight of the composition.

8. The composition of claim 5, wherein the polyamine is present in an amount of from about 0.05 to about 20% by weight, based on the weight of the composition.

9. The composition of claim 6, wherein the polyamine is present in an amount of from about 0.05 to about 20% by weight, based on the weight of the composition.

10. The composition of claim 1, wherein the oil-soluble high carbon polar modified polymer is present in an amount of from about 1% to about 30% by weight, based on the weight of the composition.

11. The composition of claim 8, wherein the oil-soluble high carbon polar modified polymer is present in an amount of from about 1% to about 30% by weight, based on the weight of the composition.

12. The composition of claim 9, wherein the oil-soluble high carbon polar modified polymer is present in an amount of from about 1% to about 30% by weight, based on the weight of the composition.

13. The composition of claim 1, wherein the oil-soluble high carbon polar modified polymer comprises maleic anhydride groups.

14. The composition of claim 1, wherein water is present in an amount of from about 5 to about 50% by weight, based on the weight of the composition.

15. The composition of claim 1, further comprising at least one colorant.

16. A method of making-up lips comprising applying onto the lips in an amount sufficient to make up the lips a composition comprising:

(a) at least one sugar silicone surfactant;
(b) a water-insoluble half acid and half amide crosslinked reaction product of (1) at least one oil-soluble high carbon polar modified polymer comprising at least one C22-C40 monomer and modified with at least one hydrophilic unit, and having a weight-average molecular weight of less than or equal to 30000 g/mol and a crystallinity of 8% to 60% and (2) at least one polyamine, wherein the reaction product forms a matrix capable of entrapping water; and
(c) water,
wherein the composition is in the form of an emulsion and wherein water is entrapped within the matrix.

17. The composition of claim 1, wherein the weight-average molecular weight of the oil-soluble high carbon polar modified polymer is from 500 to 10,000 g/mol.

18. The composition of claim 1, wherein the oil-soluble high carbon polar modified polymer comprises at least one C26-C28 monomer.

19. The composition of claim 1, wherein the oil-soluble high carbon polar modified polymer has from about 5% to about 30% hydrophilic units.

20. The composition of claim 1, wherein the oil-soluble high carbon polar modified polymer has from about 10% to about 25% hydrophilic units.

21. The composition of claim 13, wherein the oil-soluble high carbon polar modified polymer has from about 5% to about 30% maleic anhydride units.

22. The composition of claim 13, wherein the oil-soluble high carbon polar modified polymer has from about 10% to about 25% maleic anhydride units.

* * * * *